[19] United States Patent
Sachse et al.

[11] Patent Number: 4,979,124
[45] Date of Patent: Dec. 18, 1990

[54] ADAPTIVE, NEURAL-BASED SIGNAL PROCESSOR

[75] Inventors: Wolfgang H. Sachse, Ithaca, N.Y.; D. Igor Grabec, Ljubljana, Yugoslavia

[73] Assignee: Cornell Research Foundation, Ithaca, N.Y.

[21] Appl. No.: 253,837

[22] Filed: Oct. 5, 1988

[51] Int. Cl.$^5$ .................. G06F 15/46; G01N 29/00
[52] U.S. Cl. ................................ 364/507; 73/587; 364/550; 364/900
[58] Field of Search ............... 364/200, 300, 900, 513, 364/578, 801, 807, 824, 550, 507; 307/201; 381/68.2; 73/587

[56] References Cited

U.S. PATENT DOCUMENTS

| 3,103,648 | 9/1963 | Hartmanis | 364/801 |
|---|---|---|---|
| 3,111,645 | 11/1963 | Milford | 364/824 |
| 3,174,031 | 3/1965 | Hartmanis et al. | 364/824 |
| 3,222,654 | 12/1965 | Widrow et al. | 307/201 |
| 3,284,780 | 11/1966 | Clapper | 364/900 |
| 3,287,649 | 11/1966 | Rosenblatt | 328/55 |
| 3,355,713 | 11/1967 | Andreae et al. | 364/900 |
| 3,435,422 | 3/1969 | Gerhardt et al. | 364/900 |
| 3,440,617 | 4/1969 | Lesti | 364/900 |
| 3,601,811 | 8/1971 | Yoshino | 364/900 |
| 3,602,888 | 8/1971 | Nishiyama et al. | 364/900 |
| 3,950,733 | 4/1976 | Cooper | 340/172 |
| 4,254,474 | 3/1981 | Cooper | 364/200 |
| 4,326,259 | 4/1982 | Cooper | 364/715 |
| 4,414,629 | 11/1983 | Waite | 364/200 |
| 4,644,479 | 2/1987 | Kemper et al. | 364/513 |
| 4,697,242 | 9/1987 | Holland et al. | 364/513 |
| 4,719,583 | 1/1988 | Takafuji et al. | 364/807 |
| 4,752,890 | 6/1988 | Natarajan et al. | 364/300 |
| 4,752,906 | 6/1988 | Kleinfeld | 364/300 |
| 4,773,024 | 9/1988 | Faggin et al. | 364/300 |
| 4,827,418 | 5/1989 | Gerstenfeld | 364/578 |

FOREIGN PATENT DOCUMENTS

| 0765823 | 9/1980 | U.S.S.R. | 364/578 |

OTHER PUBLICATIONS

D. Robert Hay et al., "Classification of Acoustic Emission Signals from Deformation Mechanisms in Aluminum Alloys", Journal of Acoustic Emission, vol. 3, No. 3, (1984), pp. 118–129.
"An Introduction to Computing with Neural Nets"; Lippman IEEE ASSP Magazine; Apr. 1987; pp. 4–21.
"Neurocomputing: Picking the Human Brain"; R. Hecht-Nielson; IEEE Spectrum; Mar. 1988; pp. 36–41.
Wolfgang Sachse, "Applications of Quantitative AE Methods: Dynamic Fracture, Materials and Transducer Characterization," in J. D. Achenbach and Y. Rajapakse, ed. Solid Mechanics Research for Quantitative Non-destructive Evaluation (Dordrecht: Martinus Nijhoff Publishers, 1987), 41–64.
"Acoustic Emission Handbook," in Nondestructive Testing Handbook, vol. 5, Part IV (Columbus, OH: ASNT, 1988), 31–33.
Y. H. Pao, "Theory of Acoustic Emission," in idem, ed., Elastic Waves and Non-Destructive Testing of Materials (New York: Am. Soc. Mech. Engrs, 1987), 107–128.
W. Sachse and Y. H. Pao, "Locating and Characterizing Sources of Acoustic Emission," in R. B. Clough, ed., Quantitative NDE in the Nuclear Industry (Metals Park, OH: Am. Soc. Metals, 1982), 326–331.
C. B. Scruby, "Quantitative Acoustic Emission Techniques," in R. S. dSharpe, ed., Research Techniques in Nondestructive Testing (London: Acadamic Press, 1985), 141–210.
K. Y. Kim and W. Sachse, "Characteristics of an Acoustic Emission Source from a Thermal Crack in Glass", in Intl. J. Fracture, 21 (1986), 211–231.

(List continued on next page.)

Primary Examiner—Kevin J. Teska
Attorney, Agent, or Firm—Salzman & Levy

[57] ABSTRACT

A method and system for analyzing emission signals emanating from a test medium for the purpose of determining characteristics of the test medium. The system and method utilize adaptive neural processing to prognosticate future results, as well as analyzing current test results.

34 Claims, 11 Drawing Sheets

OTHER PUBLICATIONS

K. Aki and P. G. Richards, *Quantitative Seismology: Theory and Methods*, vol. 1, (San Francisco: Freeman, 1980), Chap. 3.

A. N. Ceranoglu and Y. H. Pao, "Propagation of Elastic Pulses and Acoustic Emission in a Plate: Part I. Theory; Part II. Epicentral Response; Part III. General Responses," in *ASME J. Appl Mech.*, 48 (1981), 125–147.

W. Sachse, C. Chang and K. Y. Kim, "Processing of AE Signals from Point and Extended Sources," in *Proceedings of the IEEE Ultrasonics Symposium* (New York: IEEE, 1984), 933–937.

C. P. Chen, P. N. Hsieh and W. Sachse, "Signal Processing Algorithms for AE Source Characterization," *T&AM* Report 1985-2, 1985.

T. Kohonen, *Self-organization and Associative Memory* (New York: Springer Verlag, 1989), 90–105 and 158–184.

M. A. Arbib, *Brains, Machines and Mathematics*, (New York: Springer Verlag, 1987), Chap. 4.

SOURCE COORDINATES RECOVERED R

SOURCE COORDINATES RECOVERED B

ADAPTIVE, NEURAL-BASED SIGNAL PROCESSOR

This invention was made in part with government support under grant No. MSM 8405466, awarded by the National Institute of Health; and under grant No. N00014-85-K-0595, awarded by the Office of Naval Research. The government has certain rights in the invention.

BACKGROUND OF THE INVENTION

The present invention relates to a processor for use in a signal processing system and, more particularly, to a neural-based signal processor.

Neural signal processors and networks may be utilized to make more intelligent computers and to gain new insights into how the brain functions and how people think.

Acoustic emission (hereinafter referred to as AE) signals are the transient elastic waves accompanying the sudden, localized change of stress or strain in a material. These signals result when processes, such as the formation and growth of cracks, or other inelastic deformations, phase transformations, corrosion, or the like, occur in a material. The elastic waves propagate through the medium to the surface of the specimen where they can be detected by one or more sensors.

Reliable systems for the sensing and processing of AE signals have long been sought to detect and to monitor sources of emission in a structure. The emphasis of recent research on quantitative AE techniques has been toward the development of signal processing procedures by which the detected AE signals can be analyzed to recover the characteristics of the source of emission, the properties of the propagating medium or the characteristics of the sensor with its auxiliary electronics. W. Sachse, "Applications of Quantitative AE Methods: Dynamic Fracture, Materials and Transducer Characterization", published in "Solid Mechanics Research for Quantitative Non-destructive Evaluation", J. D. Achenbach and Y. Rajapakse, Eds., Matrinus Nijhoff Publishers, Dordrecht (1987), pp. 41-64.

The focus of the processor of the invention is on the source of emission. The characteristics of an AE source refer to its location and its type. The source type is generally specified in terms of the force vector or moment tensor components modeling the source, their strength, and their temporal characteristics.

The principles by which a source of AE can be located in a structure are well established, as described in "Acoustic Emission Handbook", Vol. 5 of "Nondestructive Testing Handbook", ASNT, Columbus, Ohio (1988); Y. H. Pao, "Theory of Acoustic Emission", in "Elastic Waves and Non-destructive Testing of Materials", Y. H. Pao, Ed., AMD-Vol. 29, Am. Soc. Mech. Engrs., New York (1987), pp. 107-128; and W. Sachse and Y. H. Pao, "Locating and Characterizing Sources of Acoustic Emission", in "Quant. NDE in the Nuclear Industry", R. B. Clough, Ed., Am. Soc. Metals, Metals Park, Ohio (1982), pp. 326-331. Most common are methods based on triangulation techniques. The difference in arrival times of particular wave modes, whose speed of propagation is known, is measured from the signals detected by sensors of an array. The spatial coordinates of the source may then be recovered, provided that the number of sensors exceeds the number of unknown source coordinates by at least one and that the transducers comprising the array are not in redundant positions. With a larger number of sensors, least-squares or other optimization techniques may be applied to determine the source location which best fits the arrival time data.

An alternative to the pulse arrival measurement utilizes the arrival times of two dominant pulses in the detected signals. In that case, only three signals are required to locate a source of emission in three dimensions. A small array, for which the source is always exterior to the array, utilizes both of the aforementioned procedures to locate the source of emission. U.S. Pat. No. 4,592,034 issue May, 1986 to W. Sachse and S. Sancar for "Acoustic Emission Source Location on Plate-like Structures Using a Small Array of Sensors".

The source location procedures hereinbefore described have been demonstrated with flat plate-like specimens, cylindrical pipes and various vessels, as shown in the "Acoustic Emission Handbook" and said U.S. patent. Critical to their success is an unambiguous identification of specific wave arrivals in the detected signals. This is best facilitated from knowledge of the waveform corresponding to a particular source/receiver configuration.

In order to recover the temporal characteristics as well as the vector or moment tensor components or the spatial distribution of a distributed source, a solution to the inverse source problem must be found. This requires that the effects of the specimen boundaries and the effects of the sensor and auxiliary electronics must be deconvolved from the detected displacement signals. W. Sachse, "Applications of Quantitative AE Methods . . ."; Y. H. Pao, "Theory of Acoustic Emission Techniques", Chapter 4, in "Research Techniques in Nondestructive Testing", Vol. VIII, R. S. Sharpe, Ed., Academic Press, London (1985), pp. 141-210; and K. Y. Kim and W. Sachse, "Characteristics of an Acoustic Emission Source From a Thermal Crack in Glass", Intl. J. Fracture, 21, 211-231 (1986).

The displacement signal component $u_i$ detected at a receiver location, r, in a structure from an arbitrary point source $f(r',t)$ located at $r'$ having source volume $V_o$ can be written as:

$$u_i(r,t) = \int V_o f_j(r',t) * G_{ji}(r|r',t) dV \qquad (1)$$

where the term $G_{ji}$ represents the dynamic Green's function of the structure and the asterisk denotes a time-domain convolution. K. Aki and P. G. Richards, "Quantitative Seismology: Theory and Methods", Vol. 1, Freeman, San Francisco (1980), Chapter 3.

To obtain a solution to the inverse source problem, three requirements must be met.

(1) It is necessary that the measurements be made with a receiver whose temporal and spatial transfer characteristics are known.

(2) The dynamic Green's functions appearing in Eq. (1) are available for any particular source and source/receiver geometry.

(3) Robust signal processing algorithms are used to invert Eq. (1).

To obtain the Green's functions requires either a calibration experiment with a source of identical type as will be characterized or the solution to the elastodynamic problem of a particular source emitting in a bounded elastic medium. The first approach is often difficult or may even be impossible to carry out in most experimental situations while the second is computationally intensive for real sources operating in a real material.

Heretofore, elastodynamic calculations have been restricted to signals from a point or an extended source of arbitrary type in its near-field and operating in materials which are homogeneous, isotropic, elastic and non-attenuative. Y. H. Pao, "Theory of Acoustic Emission" and A. N. Ceranoglu and Y. H. Pao, "Propagation of Elastic Pulses and Acoustic Emission in a Plate: Part I. Theory; Part II. Epicentral Response; Part III. General Responses", ASME J. Appl. Mech., 48, 125–147 (1981).

The processing algorithms by which Eq. (1) can be inverted include least-squares schemes, such as the conjugate gradient and the singular value decomposition methods. For multi-component sources, algebraic procedures, evaluation of the radiation pattern of the emitted waves, time-domain double-iterative and frequency division methods have been used. W. Sachse, C. Chang and K. Y. Kim, "Processing of AE Signals from Point and Extended Sources", in "Proceedings of the IEEE Utrasonics Symposium", IEEE, New York (1984), pp. 933–937; K. Y. Kim and W. Sachse, "Characteristics of an Acoustic Emission Source from a Thermal Crack in Glass"; and C. P. Chen, P. N. Hsieh and W. Sachse, "Signal Processing Algorithms for AE Source Characterization", which is in preparation.

It is clear from the foregoing discussion that a rigorous solution of the inverse problem based on an elastodynamic theory represents a serious obstacle for further progress in the application of quantitative analyses of acoustic emission waveforms. It is therefore advantageous to avoid, as far as is possible, this rigorous approach for characterizing a source of emission in a material. This is especially important for field or in-service applications.

One alternative to the aforementioned deterministic procedure relies on the so-called artificial intelligence and pattern recognition approaches. D. R. Hay, R. W. Y. Chan, D. Sharp and K. J. Siddigni, "Classification of Acoustic Emission Signals from Deformation Mechanisms in Aluminum Alloys", J. Acoustic Emission, 3, 118–129 (1984). In these, a system is trained by transforming the signals into an arbitrarily chosen descriptor or feature space whose components are empirically related to specific features of the AE source to be characterized. The difficulty of this approach is that it is not based on any elastodynamic theory and hence it does not enable a quantitative evaluation of an AE source in terms of variables characterizing the physical processes involved.

Systems that have previously been invented for visual and audio pattern recognition applications are described in U.S. patents issued to F. Rosenblatt (U.S. Pat. No. 3,287,649); and L. Cooper and C. Elbaum (U.S. Pat. Nos. 3,950,733; 4,254,474; and 4,326,259). Such systems may learn and may classify patterns, but they cannot be used to solve forward and inverse problems related to wave phenomena. These problems are essentially linear. Therefore, the aforementioned systems, with threshold elements at their outputs (which results in a non-linear operation), cannot be applied in a straightforward manner. Furthermore, the learning algorithm described in the aforementioned patents (Cooper et al) do not lead to a convergent learning of waveforms.

The principal object of the invention is to provide an alternate means by which the aforedescribed problems can be circumvented.

An object of the invention is to provide a neural-like signal processing system which utilizes an approximate method and which resembles the acoustic signal analysis procedure used by primitive intelligent beings. T. Kohonen, "Self-organization and Associative Memory", Springer Verlag, New York (1984) and M. A. Arbib, "Brains, Machines and Mathematics", Springer Verlag, New York (1987).

Another object of the invention is to provide a neural signal processor which functions efficiently, effectively and reliably as an intelligent processing system.

Still another object of the invention is to provide a neural signal processor suitable for use in a laboratory or a personal computer system.

Yet another object of the invention is to provide a neural signal processor which is completely independent of any elastodynamic theory, although it is capable of yielding quantitative results.

Another object of the invention is to provide a neural signal processor which utilizes the detailed features of a detected signal and wherein the entire procedure depends only on that information presented to the system during the learning process.

Still another object of the invention is to provide a neural signal processor which may form the basis for new instrumentation having application to many other intelligent non-destructive materials test and monitoring systems, as well as to systems with medical and seismological applications.

SUMMARY OF THE INVENTION

The neural-like processing system of the invention operates in two characteristic modes called the learning and processing modes. As in quantitative AE measurements, when the neural-like processing system is operating in the learning mode, it accepts and "memorizes" experimental AE waveforms. To these are appended relevant data about the source, such as its location, components, time function or strength.

In the analysis mode, information-limited AE signals are processed to recover the characteristics of the source according to the previously learned data derived from the phenomenon being monitored.

Although the procedure resembles that used to solve inverse problems, in the neural processing scheme there is no elastodynamic basis directly or implicitly imbedded. This is a fundamental difference between these two signal processing approaches. Therefore, the use of a neural processing approach could become the basis of a wide variety of other non-destructive materials measurements.

The neural signal processor of the invention analyzes elastic wave signals to obtain an optimal solution to inverse source problems. Using a simulated intelligent system which resembles the structure of a neural network and an acoustic source with its associated field of elastic waves in a plate, a set of pattern vectors is generated. The memory of the system is formed through a learning process in which a systematic series of experiments is presented to the system. In the experiments described herein, the system was trained using simulated acoustic emission signals generated by a normal force acting on a thick plate to which were appended information about the source related to its location and characteristics. Using such a trained system, the characteristics of an unknown source may be recovered from the acoustic signals emitted by it. It is also shown that the acoustic signals corresponding to an arbitrary source may be synthesized from the memory without using any elastodynamic theory.

In accordance with the invention, a method for processing a signal to train a system for subsequent recovery of an unknown characteristic thereof comprises the steps of applying signals from a plurality of known sources to a medium, detecting the signals propagated through the medium and generating a pattern vector representative of the system, and applying the pattern vector to a memory for development thereof.

The unknown characteristic may be a signal representative of a source or a signal representative of the medium or a signal representative of a sensor.

Moreover, the unknown characteristic may be a signal representative of the source and the medium or a signal representative of the medium and the sensor or a signal representative of the source and the sensor.

The pattern vector comprises detected signals and characteristics of descriptors appended thereto. The characteristics of descriptors may comprise source signal characteristics, medium signal characteristics or sensor signal characteristics.

The step of applying the pattern vector to a memory for development thereof further comprises detecting differences between the pattern vector and the recall of the memory to the signal and generating a novelty signal representative thereof, and applying the novelty signal to further develop the memory.

Also in accordance with the invention, a method for processing a signal to train a system for subsequent recovery of an unknown characteristic thereof comprises the steps of applying signals from a plurality of known sources to a medium, detecting the signals propagated through the medium and generating a pattern vector representative of the system, applying the pattern vector to a memory for development thereof, applying a probe signal representative of at least one unknown characteristic of a system to the memory, and processing the probe signal in association with contents of the memory to recover the unknown characteristic of the system.

The unknown characteristic may be a signal representative of a source or a signal representative of the medium or a signal representative of the sensor or any combination of signals representative of the source, the sensor and the medium.

The step of applying the pattern vector to a memory for development thereof further comprises detecting differences between the pattern vector and the recall of the memory to the signal and generating a novelty signal representative thereof, and applying the novelty signal to further develop the memory.

Also in accordance with the invention, a method for processing a signal to train a system for subsequent recovery of unknown characteristics thereof, comprises the steps of applying signals from a plurality of known sources to a medium, detecting the signals propagated through the medium and generating a pattern vector representative of the system, applying the pattern vector to a memory for development thereof, applying a probe signal representative of at least two unknown characteristics of a system to the memory, and processing the probe signal in association with contents of the memory to recover the unknown characteristics of the system.

BRIEF DESCRIPTION OF THE DRAWINGS

In order that the invention may be readily carried into effect, it will now be described with reference to the accompanying drawings wherein.

DETAILED DESCRIPTION OF THE PREFERRED EMBODIMENT

Figure 1:
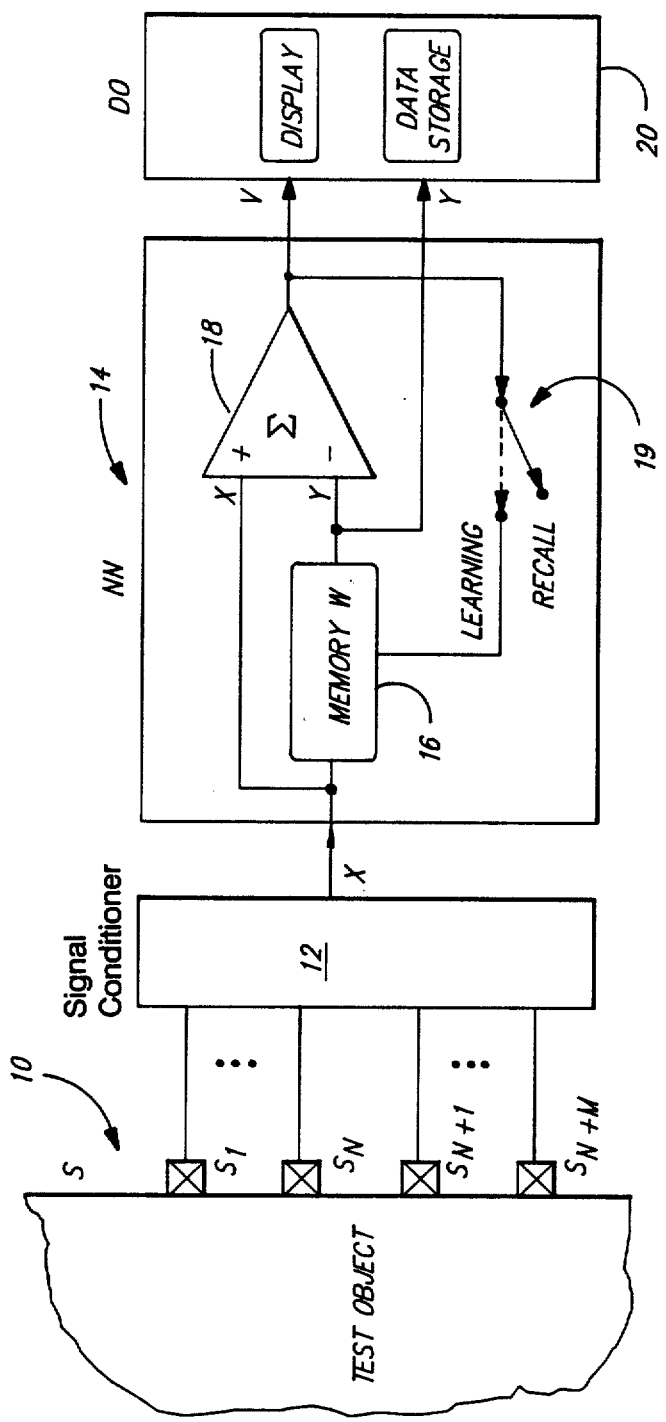
FIG. 1 is a schematic block diagram of an embodiment of the adaptive, neural-based signal processing system of the invention.

In an ideal AE detection system, a particular displacement, or velocity, signal $u(r,t)$ is detected by a discrete number N of sensors and processed by amplifiers into the set of voltage signals $\{v(n,t); n=1, \ldots, N\}$, which are usually recorded only over a finite time interval $\{0,T\}$. It is important to remember that in practice only incomplete, band-limited and noise-corrupted information is obtained about the displacement field. Therefore, it should not be expected that a source of emission can be precisely characterized, even if a solution to the inverse problem stated by Eq. (1) can be found.

On the basis of experimental observations, and from Eq. (1) it is assumed that a particular acoustic emission event can be described by a set of measurement fields involving signal displacements (or velocities) and forces: u(r,t); f(r,t). In principle, these fields are linearly related, but the mapping is generally not known. A detailed specification of this mapping is avoided. Rather, it is only assumed that it ca be indirectly and partially described by a set of K experimental observations given by $$\{v_k(n,t); g_k; n=1,\ldots,N; t\in(0,T); k=1,\ldots,K\} \quad (2)$$

In this Equation (2), n and k are, respectively, the sensor index and the waveform record index. The term $g_k$ represents the available, partial information about the source, f, which by means of the wavefield u gives rise to the signals, $v_k(n,t)$. For the sake of convenience, a pattern vector, $$X_k = \{v_k(1,t),\ldots,v_k(N,t); g_k\} \quad (3)$$

is introduced, which represents the concatenation of all the experimental data sets corresponding to the $k^{th}$ experiment. All such treatments of the data are permitted provided that they are equivalently carried out on all data sets.

To obtain a quantitative physical description of the phenomenon, the source components, $g_k$, must be characterized by signals corresponding to the source quantities of interest. Otherwise, the resulting description will be empirical.

Next, a system is constructed by which any new series of signals can be represented by a mixture of all previously presented series. The latter comprise the recall vector while the difference between the signal and the mixture is the novelty vector.

If a series of signals, similar to any one of the previously presented signals is then presented to the system, it can be expected that the recall vector should resemble that signal most similar to it. Such a processing method is called an auto-associative recall and it has previously been applied to pattern recognition problems. T. Kohonen, "Self-organization and Associate Memory". In order to perform the auto-associative recall, the processing system must be able to remember the first signal and be able to apply the novelty of all succeeding signals to build up the memory.

The operation of the neural processing system can be illustrated if two reference signals $X_1$ and $X_2$, are considered. Using a Gram-Schmidt orthogonalization, the vector $X_2$ can be represented by two components, one which is aligned with $X_1$ and the second which is orthogonal to $X_2$. T. Kohonen, "Self-organization and Associative Memory". The latter is determined by:

$$V_2 = X_2 - \frac{(X_2, X_1)}{\|X_1\|^2} X_1 \quad (4)$$

The orthogonal basis for the representation of the signals can be found by repeating this process. That is, $$V_1 = X_1$$

$$V_2 = X_2 - \frac{(X_2, V_1)}{\|V_1\|^2} V_1$$

.
.
.

and after $k$-steps, $V_k = X_k - \sum_{i=1}^{k-1} \frac{(X_k, V_i)}{\|V_i\|^2} V_i \quad (5)$

.
.

The component $V_k$ in these equations cannot be expressed by the previous signals and it therefore represents the novelty. The sum in the general equation, Eq. (5), represents that component of the vector $X_k$ which can be expressed, or predicted in terms of all previous reference patterns, and it therefore corresponds to the recall vector. This vector is given by:

$$Y_k = \sum_{i=1}^{k-1} \frac{(X_k, V_i)}{\|V_i\|^2} V_i \quad (6)$$

A rule for constructing the recognition system can be obtained if Eq. (6) is rewritten in the general matrix form:

$$Y = W X \quad (7)$$

The recall vector, Y, is a by-product of the orthogonalization procedure and the memory matrix, or weighting function, after k experiments. W is defined by the expression $$W = \sum_{i=1}^{k-1} \frac{V_i V_i^T}{\|V_i\|^2} \quad (8)$$

It is seen that the weighting function is determined by the auto-correlation function of the novelty vector. With this notation, the novelty component, after k experiments, can be expressed by the equation:

$$V_k = X_k - Y_k = X_k - X_k = (I - W)X_k \quad (9)$$

According to Eqs. (8) and (9) the orthogonalization process is performed by a discrete adaptive system with the input, $X_k$, output $V_k$, and response function, W. The latter is adaptively modified after each set of signals presented to the system, according to the rule:

$$\Delta W = \frac{V_k V_k^T}{\|V_k\|^2} \quad (10)$$

Unfortunately, this simple orthogonalization scheme is sensitive to small disturbances in the input signals, $X_k$. With real signals the processing can, in fact, become unstable after only a modest number of learning steps. A stabilization can, however, be achieved by continuously and adaptively changing the memory, W, in non-dimensional time, according to the modified rule:

$$V_k = X_k - W X_k = X_k - Y_k \quad (11)$$

$$\frac{dW}{dt} = V_k V_k^T$$

In this way, the system operates similarly to a neural network. T. Kohonen, "Self-organization and Associative Memory". The learning of the series of reference signals is begun with W=0 and it develops with each stationary input vector, $X_k$, until the norm of the novelty vector $|V_k|$ falls below the noise level of the signal after each presented signal, $X_k$, the matrix W includes the term corresponding to:

$$\frac{V_k V_k^T}{\|V_k\|^2}$$

The adaptive system described by these equations is shown schematically in FIG. 1, described in greater detail hereinbelow. The novelty, V, of each presented pattern is fed back into the memory to cause adaptive changes continuously in the weighting function W.

Since the adaptive learning described here corresponds to a Gram-Schmidt orthogonalization process, the initial patterns presented to the system have a greater influence on the formation of the memory than those presented later. This corresponds to a greater statistical weight assigned to them. In an experiment, however, an equal statistical weight should be assigned to each of the presented K patterns. This can be achieved by modifying Eq. (11) as follows:

$$\frac{dW}{dt} = \frac{1}{K} \sum_{k=1}^{K} V_k V_k^T = R_V \qquad (12)$$

The generator of memory in this case is the auto-correlation function $R_V$ of the output novelty signal. The learning process described by Equation (12) leads to a memory which has been shown to minimize the mean square error of the recall. R. Penrose, "A Generalized Inverse for Matrices", Proc. Cambr. Philos. Soc., 51, 406–413 (1955) and R. Penrose, "On Best Approximate Solutions of Linear Matrix Equations", Proc. Cambr. Philos. Soc., 52, 17–19 (1965). For a pattern vector of modest dimension, of order $10^2$, the numerical procedure can be efficiently carried out on a personal computer.

The complete correlation function $R_V$ need not be exactly evaluated if the weighting function is adaptively modified at each step according to $$\frac{1}{K}(V_k V_k^T)\Delta t,$$

where $\Delta t$ is the step size of the learning process. This requires that the learning process must be sufficiently slow, so that all K patterns of the learning set are learned in each iteration step under approximately equal conditions. Such a learning process assures equal statistical weight of the presented patterns. In addition, it is convenient to use normalized input pattern vectors in order to avoid numerical problems arising from large and small data values.

The learning process, by which the memory matrix is formed, can be accelerated by modification of the adaptation or procedure represented by Eq. (12). It can be shown from a dimensional analysis that for a constant presented pattern, the amplitudes of the novelty vector, V tend to zero as $1/t$, if the term $V V^T$ is used. In contrast, the novelty vector amplitude tends to zero as $e^{-t}$ or $e^{-t^2}$, if the terms $V X^T$ or $V X^T t$ are applied in Eq. (12), where t denotes the non-dimensional time of the learning process. These considerations are of special importance when optimizing the processing algorithms for large dimensioned pattern vectors. The adaptation constants, t or t/k, must be taken in accordance with the stability of iteration desired.

The system described by Eqs. (11) and (12) was implemented in software executed by a laboratory minicomputer. The simulated signal patterns consisted of 64-point waveforms. During the experimentation of real measurement situations, 150-point AE signals were used. It was found that sufficiently accurate adaptation could be attained in the iteration procedure in twenty steps, if a step size of $\Delta t = 1.0$ were used in the iterations.

Figure 2A:
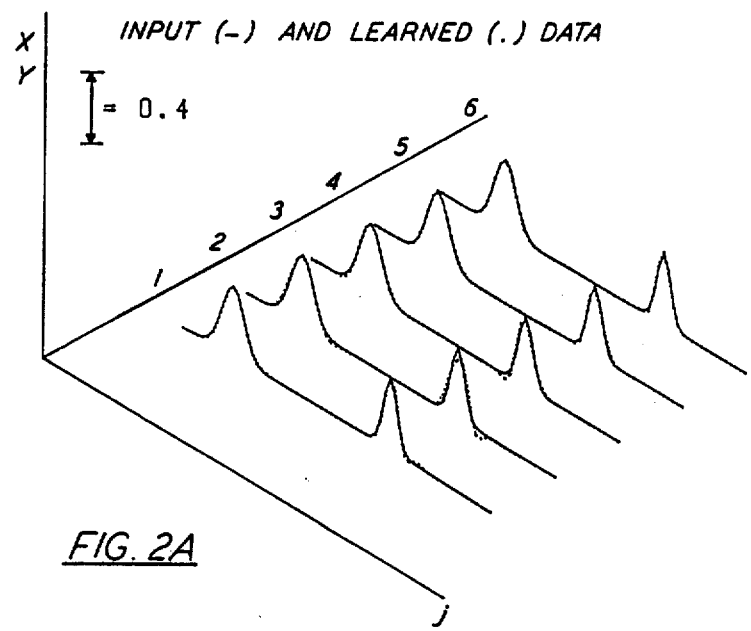
FIG. 2A is an example of series of simulated learning patterns and the corresponding learned result.

FIG. 2A shows an example of a series of simulated learning patterns, indicated by solid lines, and the corresponding learned recall, indicated by dotted lines. The overlap between these results is almost perfect, resulting in almost indistinguishable signal records shown in FIG. 2A. Good agreement between the learned signals, X, and the recalled signals, Y, confirm the correctness of the learning process.

Figure 2B:
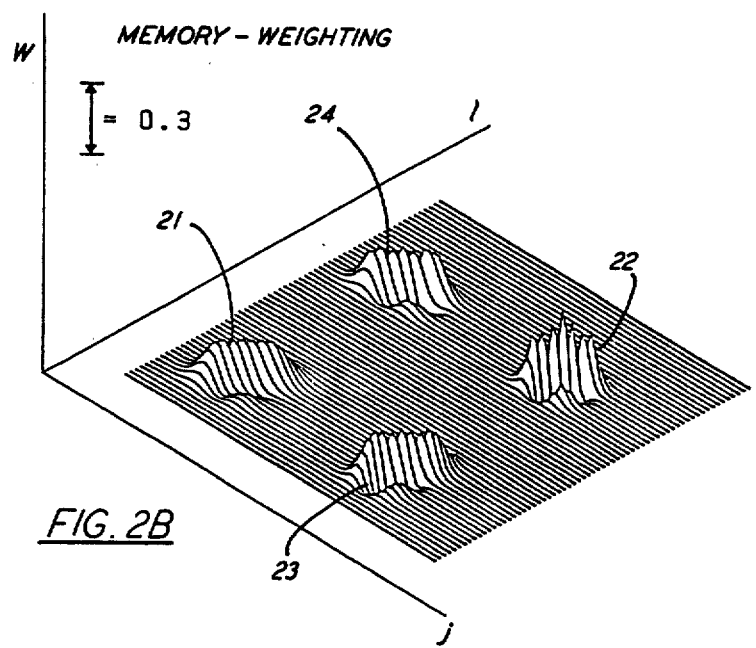
FIG. 2B illustrates the memorized weighting function.

FIG. 2B depicts the memorized weighting function W. It consists of four characteristic regions, corresponding to the correlations of two pulses of presented data. The lower left and upper right portions 21 and 22, respectively, of FIG. 2B correspond to the auto-correlation of the left and the right pulses in the presented patterns, respectively. The lower right and upper left portions 23 and 24, respectively, of FIG. 2B correspond to the cross-correlation of both pulses appearing in the waveforms.

During the recall calculation, the weighting matrix W is multiplied by the input vector X. If a signal possesses a non-zero value at a point where a row in the correlation matrix also has a non-zero value, then a non-zero contribution to the recall vector is obtained. In the auto-associative recall, contributions are composed of two parts; the first resulting from the auto-correlation part and the second by the cross-correlation of W. If a portion of the input signal is missing, the cross-correlation operation can recover this information during the recall. This result is a fundamental property of the associative character of a neural-like processing system.

Figure 2C:
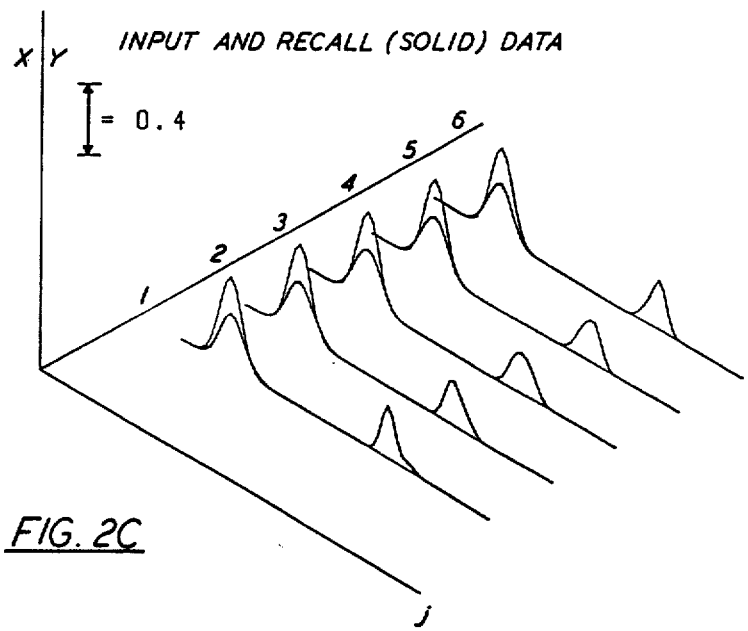
FIG. 2C is an example of the recalled sequence of signals.
Figure 2D:
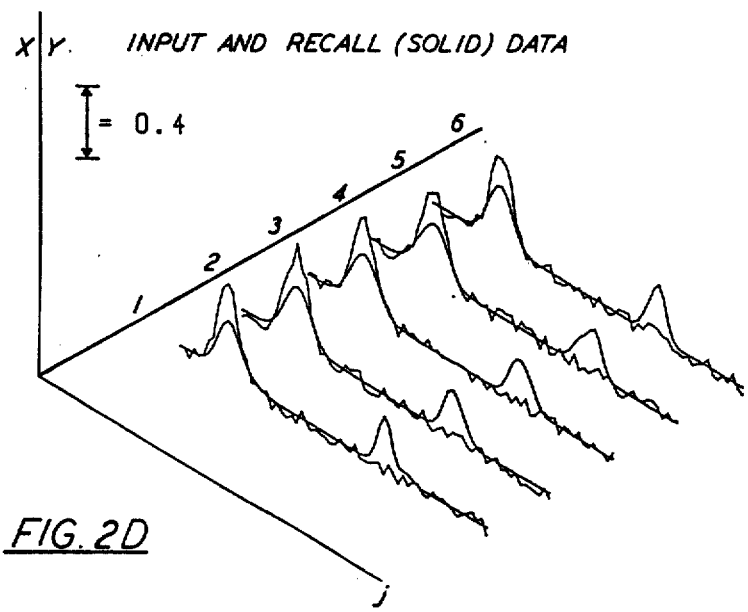
FIG. 2D is another example of the recalled sequence of signals.

FIGS. 2C and 2D are two examples of the reference sequence of signals, which were first modified and subsequently noise-corrupted, and the corresponding recalled signals. FIG. 2C shows one pulse input and two pulse recall in solid lines and FIG. 2D shows one pulse noise-corrupted input and the corresponding recall, in solid lines. It is seen that during the recall process the neural system can supply the missing portions of the signals and can efficiently increase the signal-to-noise ratio of a signal. This indicates that the neural network is similar to a matched or an optimal filter. I. Grabec, "Optimal Filtering of Transient AE Signals", in "Ultrasonics International '85: Conference Proceedings", Butterworth Scientific, Ltd., Surrey, U.K. (1985), pp. 219–224 and I. Grabec, "Development of a Force Transducer for AE Analysis", ibid, pp. 596–600.

In order to demonstrate the capabilities of the system of the invention, two sets of experiments which utilized simulated acoustic emission signals are now described. It should be understood, however, that other sources, including, but not limited to magnetic, electromagnetic, radio, sonar, piezoelectric signals and the like can also be used within the scope of the present invention. The first was a source location problem. The second involved, in addition, the recovery of the characteristics of a simple, one-dimensional vector source corresponding to a normal force acting on the surface of a structure.

The experimental setup consisted of a 1-inch, or 25 mm, thick, flat plate, thirty inches, or 0.75 m, on edge, with an array of miniature, broadband piezoelectric sensors mounted on it. The active area of the sensors was 1.3 mm in diameter. The AE events were simulated by the impact of a steel ball, or by the fracture of a pencil lead, on the surface of the plate. The signal from each sensor was amplified by 40 db and recorded in one channel of a multi-channel waveform digitization system. The start of the waveform digitization was synchronized by a pulse generated by one of the signals from a separate waveform digitizer. A digitization rate of either 2 MHz, or 5 MHz, was used in all the experiments, depending upon the frequency characteristics of the source.

Alternate points were deleted in the 1024-point waveforms of the input signals until the waveforms were sufficiently short, so that the data from the various sensors could be concatenated to obtain a compound AE signal 128 points long. Another 22 points of data, corresponding to specific encoded information about the source, was appended to this signal. The final dimension of the resulting pattern vector which was presented to the processing system was 150 points long; this being dictated by the memory capacity of the available processing system. Three sets of experiments with different sources and sensor configurations are hereinafter described. These were chosen to illustrate some of the capabilities of this processing approach.

Figure 3A:
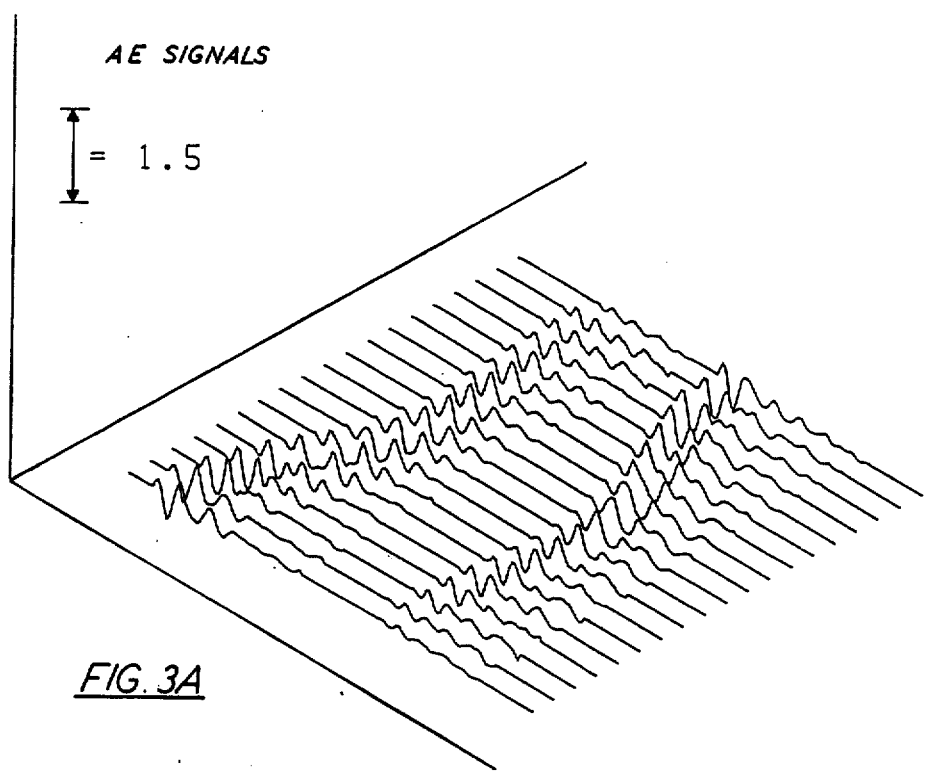
FIG. 3A shows AE signals detected by two sensors with the source located at various points between the sensors.
Figure 3B:
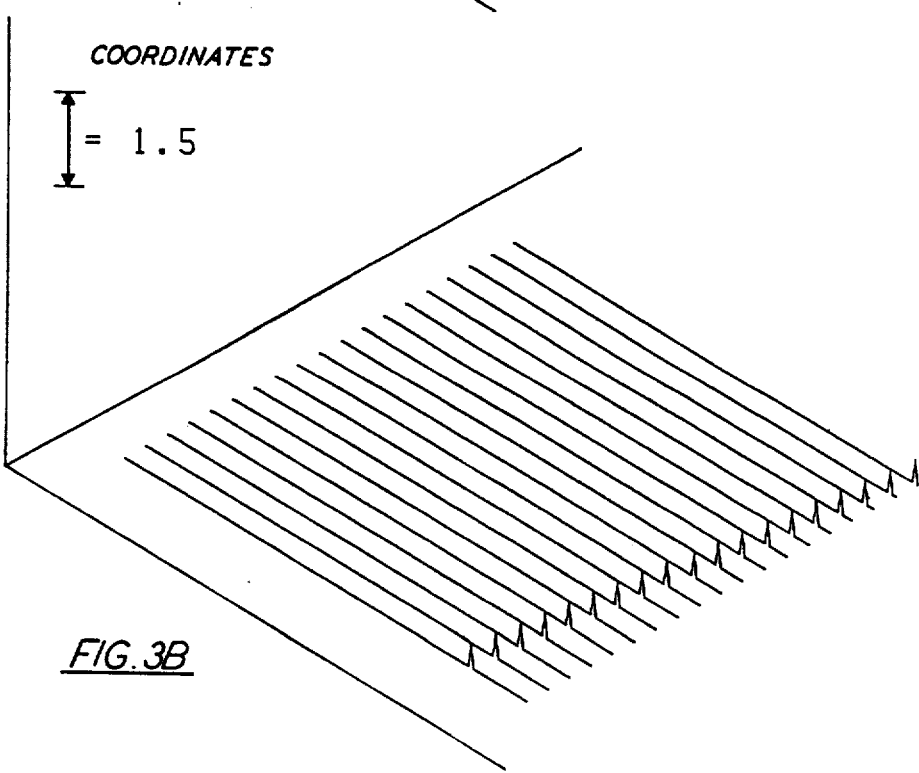
FIG. 3B shows the coded source portion, or coordinate, data.

In the first set of experiments, the operation of a linear source location system was investigated. Two sensors were spaced 20 inches, or 0.5 m, apart on a line parallel to one edge of the plate. The AE was simulated by the impact of a steel ball of diameter $\Phi=8$ mm dropped from a height of 5 mm. During the learning phase, the source was activated at positions 1 inch, or 25 mm, apart, along a line between the two sensors. The detected signals are shown in FIG. 3A by curves 3A1, ..., 3A19. The source position was encoded by a constant non-zero value at a particular point of the last 22 points of the pattern vector, as shown in FIG. 3B by the curves 3B1, ..., 3B19.

Figure 3C:
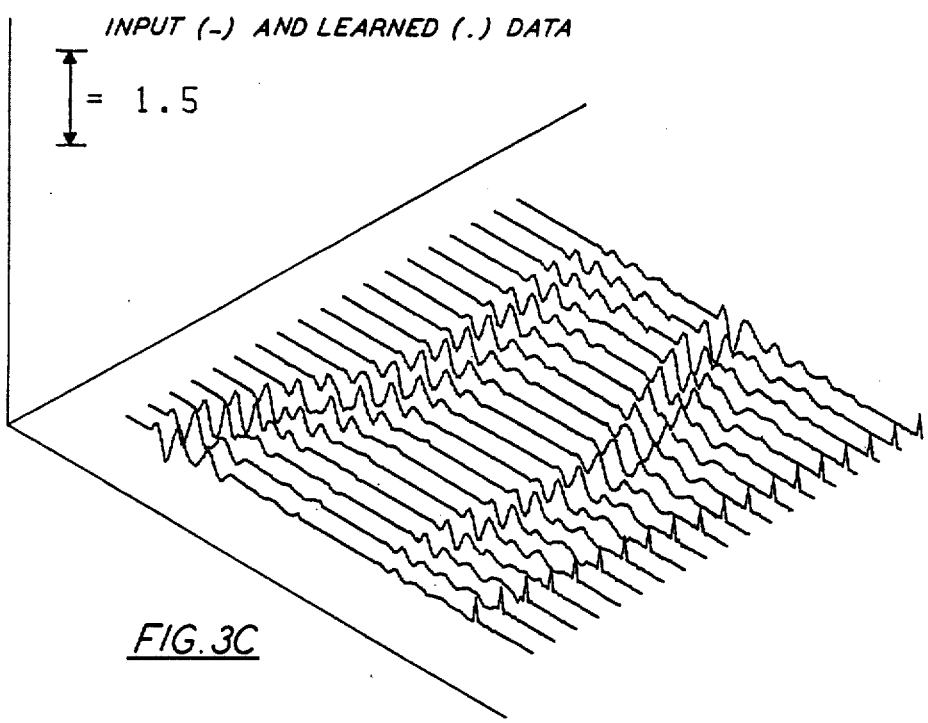
FIG. 3C discloses input vectors comprising AE signals and source location data for the linear location problem.

The completed set of the learning vectors is shown as solid lines in FIG. 3C by the curves 3C1, ..., 3C19. The input curve 3C1 was obtained by superimposing curves 3A1 and 3B1. Similarly, all 3C curves were obtained by superimposing respective 3A and 3B curves. During the learning procedure, the learned recall vectors achieve essentially the same values as the input vectors. This is illustrated by the dotted lines superimposed on the original input vectors in FIG. 3C, which shows input vectors comprising AE signals and source location data for the linear location problem. The square norm of the novelty vector was found to be less than $10^{-3}$ after twenty steps, which corresponds to an average value of less than $10^{-5}$ per component. This demonstrates that a correct adaptation of the system has occurred during the learning phase of the system.

Figure 3D:
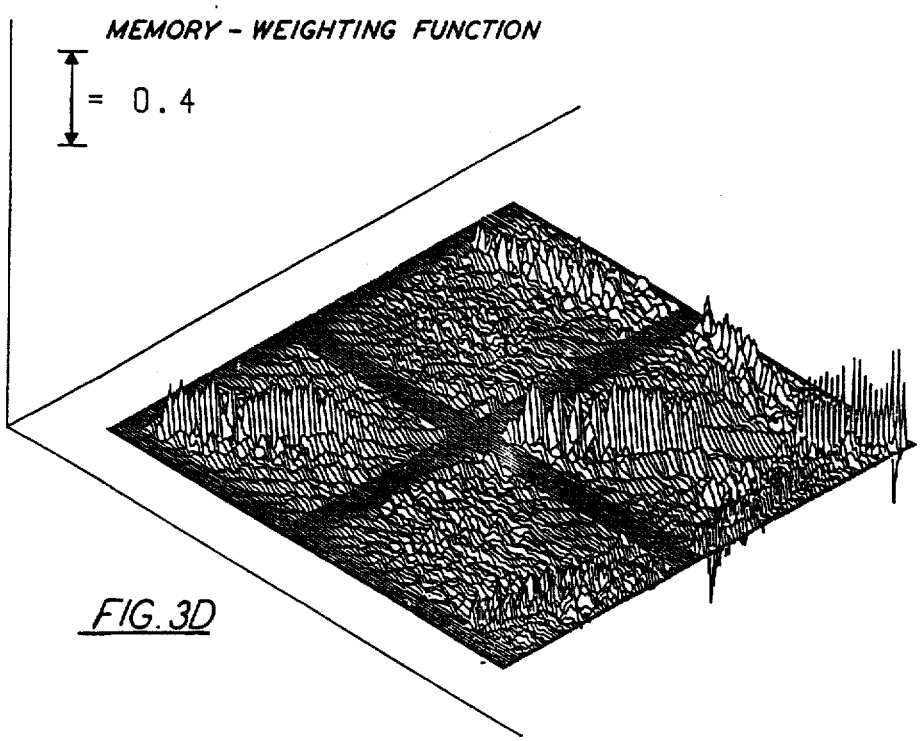
FIG. 3D discloses the weighting function generated by signals in the linear location problem.

The weighting function which was formed in the memory during the learning is shown in FIG. 3D. There are nine characteristic regions in this memory which correspond to the auto- and cross-correlations of the data from the two sensors and the characteristics of a one-dimensional source location. Each region is of specific importance for the operation of the system during the recall mode, as hereinbefore described.

With the memorized weighting function W, the system can be used for the analysis of experimental data. For this purpose, the feedback to the memory must be turned off. In the first test, the input AE signals presented to the system were those used for the learning set, but without the coded information about the location of the source, as shown in FIG. 3A.

Figure 4A:
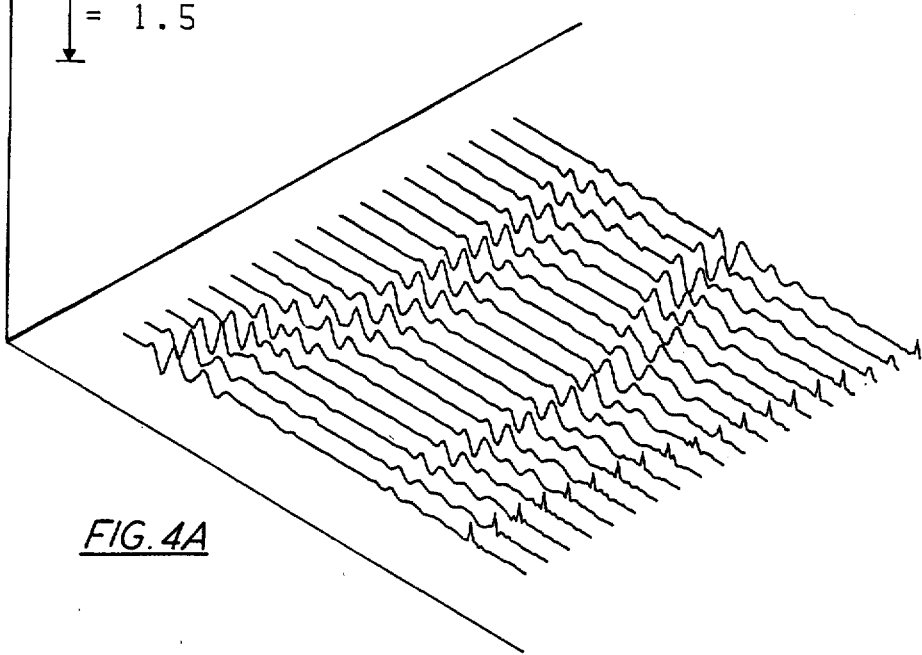
FIG. 4A shows the result obtained using the input data shown in FIG. 3A with the recovered source location.

In the corresponding recall signals, the source coordinates were all correctly recovered from the memory information. This is shown in FIG. 4A. The signal 4A1 was recovered from the input 3A1. When the recalled coordinates are compared with the un-encoded coordinates presented in FIG. 3B, it is noted that the recall is not exact, but slightly noise-corrupted. The coordinate positions are, however, correctly recovered from the cross-correlation between the signals and the coordinates in the memory matrix W.

The contribution to the recall vector from the autocorrelation of the coordinate portion is missing at those points in the coordinate portion where the input signal has zero amplitude. The source location position is therefore not precisely recovered, but is, instead, noise-corrupted. The contributions of the cross-correlation between the coordinates and the AE signals are also missing in the AE portions of the recall vector. The noise in the output is, however, less apparent because of the diminished strength of the coordinate portion of the input data. In spite of the noise present in the recall, the source position can still be satisfactorily estimated from the recalled vectors.

Figure 4B:
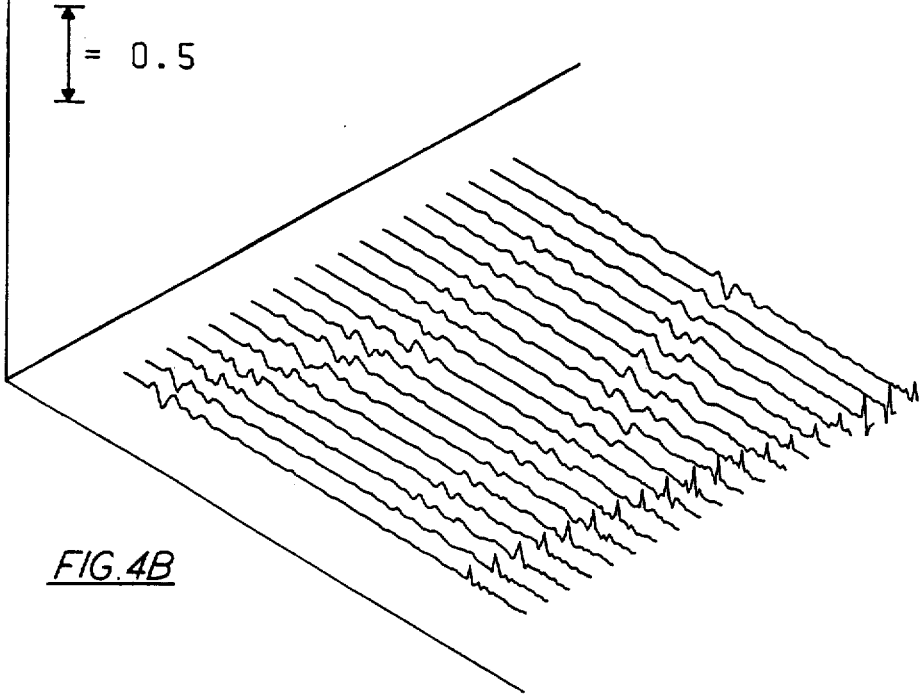
FIG. 4B discloses the obtained recall using the input data shown in FIG. 3B with the recovered AE signals.

To investigate the efficacy of the processing system to recover waveforms corresponding to a particular source location, only the coordinate data shown in FIG. 3B were presented to the system. The obtained recall is shown in FIG. 4B. The signal 4B1 was recovered from the input 3B1. It is seen that because of the missing contribution of the input AE signals, the original signals are only partially recovered from the cross-correlation portion of the AE signals and the source signals in the memory matrix. Since the AE signals represent 128 out of 150 points of the total pattern length, their recall by a smaller number of coordinate points is less reliable than recalling the fewer coordinate points from a longer signal portion. Nevertheless, the recall is able to recover the principal features of all the AE signals.

Figure 5A:
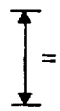
FIG. 5A shows the recall vectors obtained in a repeat set of linear location experiments.
Figure 5A:
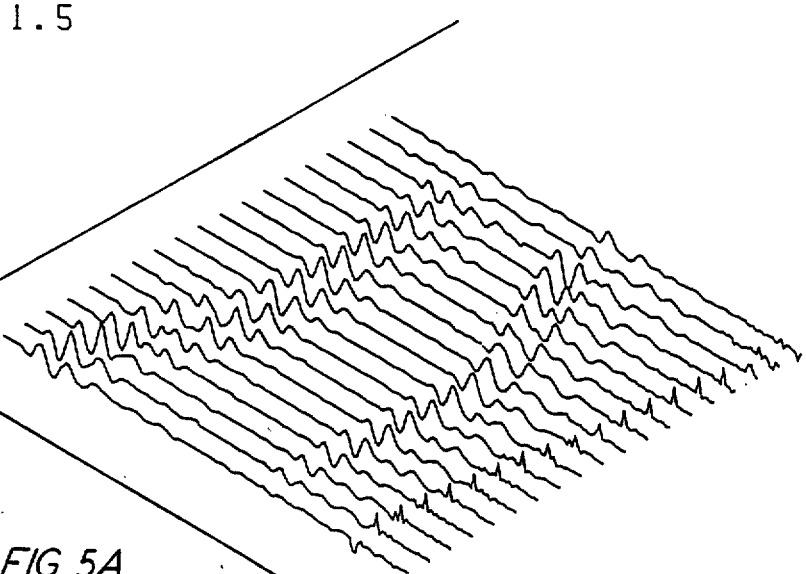

In a repeated series of experiments, the signals measured at the same point differed slightly from the previous ones because of experimental variations and noise. FIG. 5A shows the recall vectors obtained from the AE signals recorded during the second run of the experiment. The recall does not appear to be as good as that obtained from the first signal set; but, in most cases, the system can still correctly recover the source position. The largest discrepancies appear in the initial and final records 5A1, 5A19 where the signal from one of the two sensors is markedly weaker than that of the other. It is also noted that, because of geometric wave dispersion effects, the triggering of the waveform recorders is not as precise as for the cases in which the source is located near the center of the monitored region.

Figure 5B:
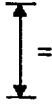
FIG. 5B discloses the recall obtained from signals excited at source location points between the points of the learning set.
Figure 5B:
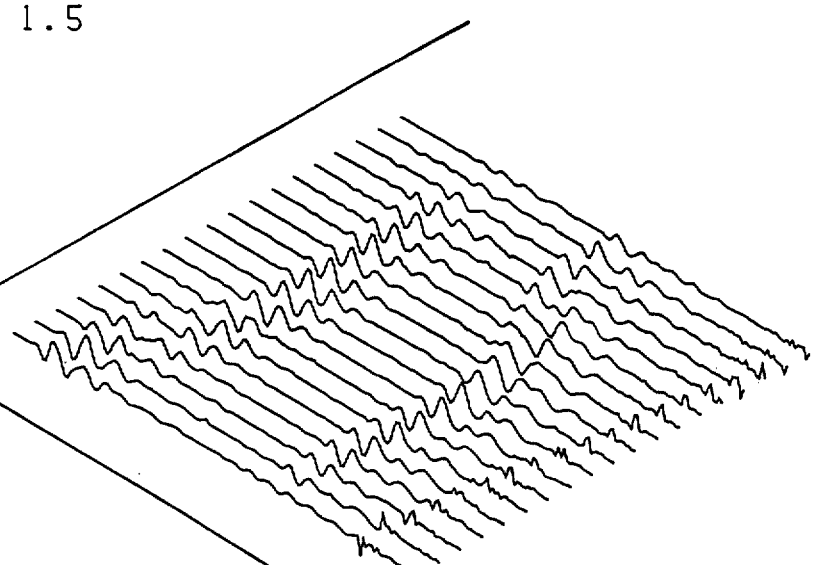

A third run of the aforedescribed experiment was carried out by dropping the ball in the middle of the intervals used to train the system in the first run. The series of recalled vectors obtained from the corresponding AE signals is shown in FIG. 5B. The signal 5B1 was obtained by the source in the middle of the first interval between the sensors. Although in these data the recalled source location exhibits several peaks, it is the largest of these which correctly corresponds to the actual location of the source. It may be expected that similar results will be observed with the other experimental arrangement if the points used in learning are separated more than a characteristic wavelength.

Figure 6A:
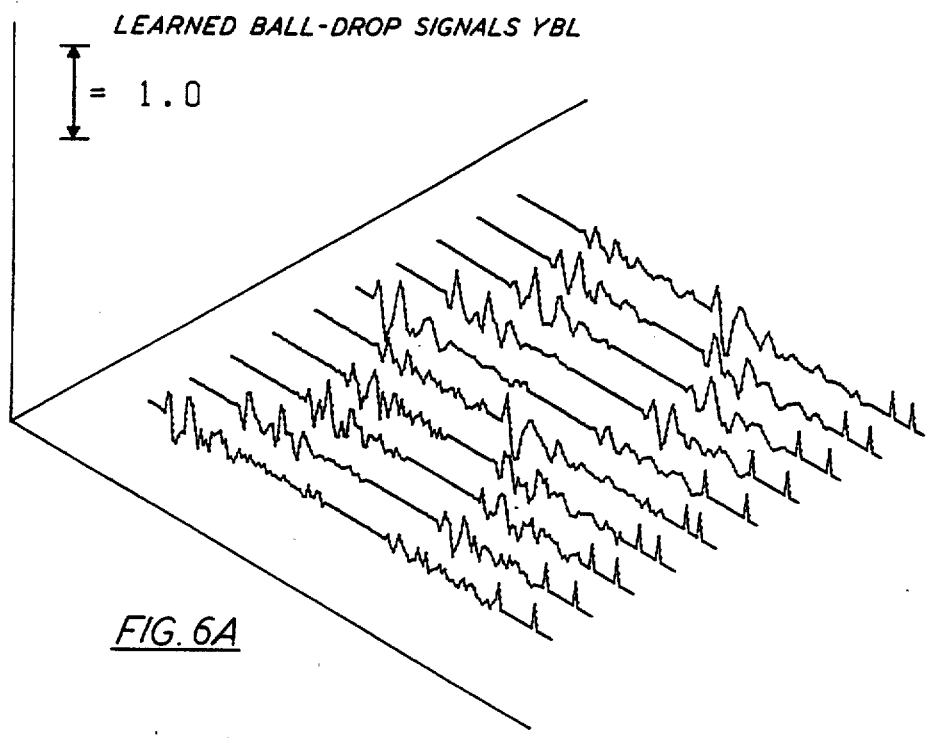
FIG. 6A shows the pattern vectors obtained by dropping 4 and 6 mm diameter balls at various locations along a line.

The second series of experiments was performed in order to investigate the capability of the system to recognize, in addition to the location of the source, some other characteristic of the AE source. For this purpose, the same experimental arrangement as described was used, but here the AE source corresponded to one of two balls of different diameters, $\phi = 4$ and 6 mm, dropped onto the plate. FIG. 6A shows a normalized, representative set of records or pattern vectors obtained by dropping 4 and 6 mm diameter balls at various locations along a line. The solid lines again represent the input data while the dotted line is the recall vector. Due to very accurate learning, both sets of curves practically overlays.

Figure 6B:
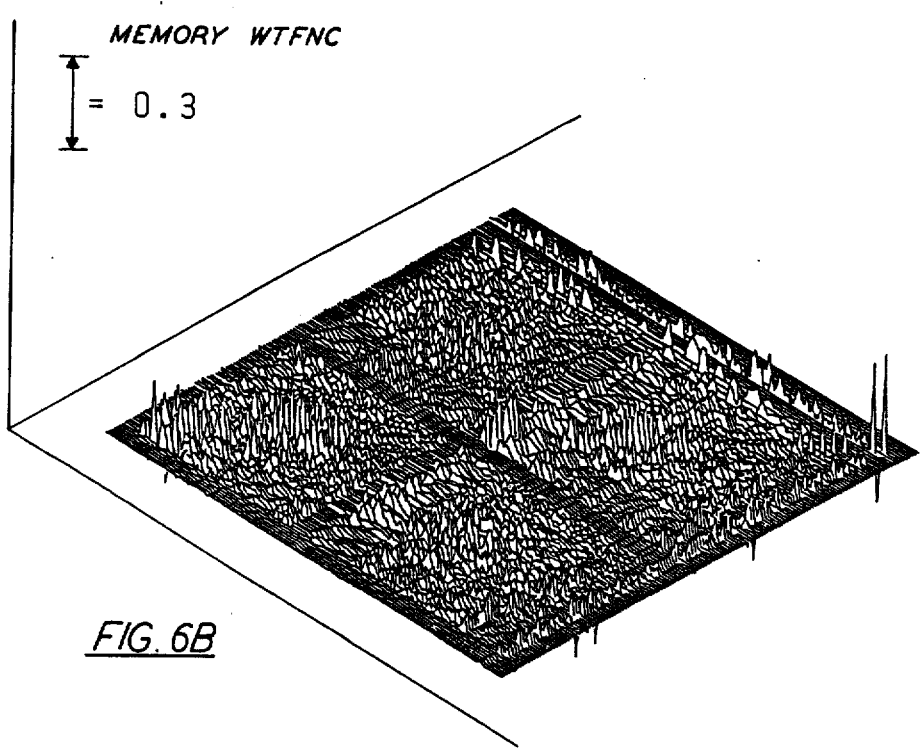
FIG. 6B indicates the memorized weighting function.

In this example, the source was encoded by two descriptors a and b (FIG. 6A), one (a) corresponding to the position coordinate and the other (b) to the diameter of the ball. This information appears as two peaks at different positions on the latter portion of each record. The corresponding memory matrix or memorized weighting function is shown in FIG. 6B. The learning process in this case was faster than in the previous experiment, because of the smaller number of patterns needed to learn the system, but the rate of convergence was the same.

Figure 6C:
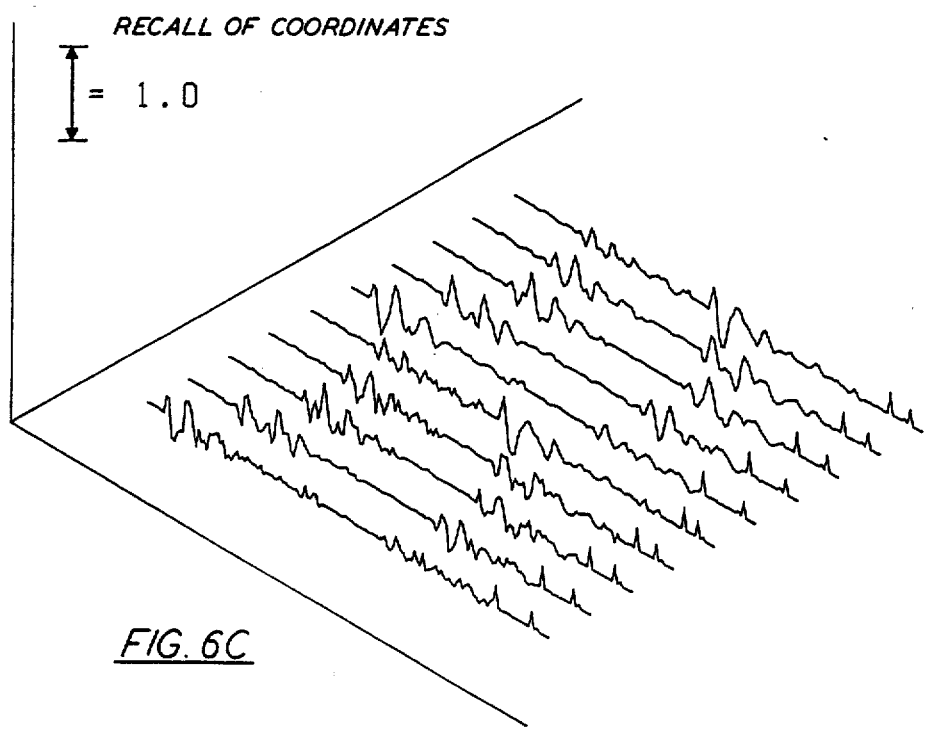
FIG. 6C shows the recalled signals.

After the learning mode, the signal portion of the patterns was again presented to the system. The recalled signals are shown in FIG. 6C by the curves 6C1, ..., 6C10. It is seen that the position of the source is recovered precisely. The recall of the second coordinate specified by the b-descriptor corresponding to the ball size, shows a weak mismatch, which is a consequence of the similarity between the signals excited by the two different-sized balls. The most significant difference between the signals of the two balls is in the signal amplitudes. Unfortunately, the amplitude information was lost, because the input data was normalized during the pre-processing. To avoid this problem, it is suggested that the signal strength should be encoded as an additional feature in the input vector.

Figure 6D:
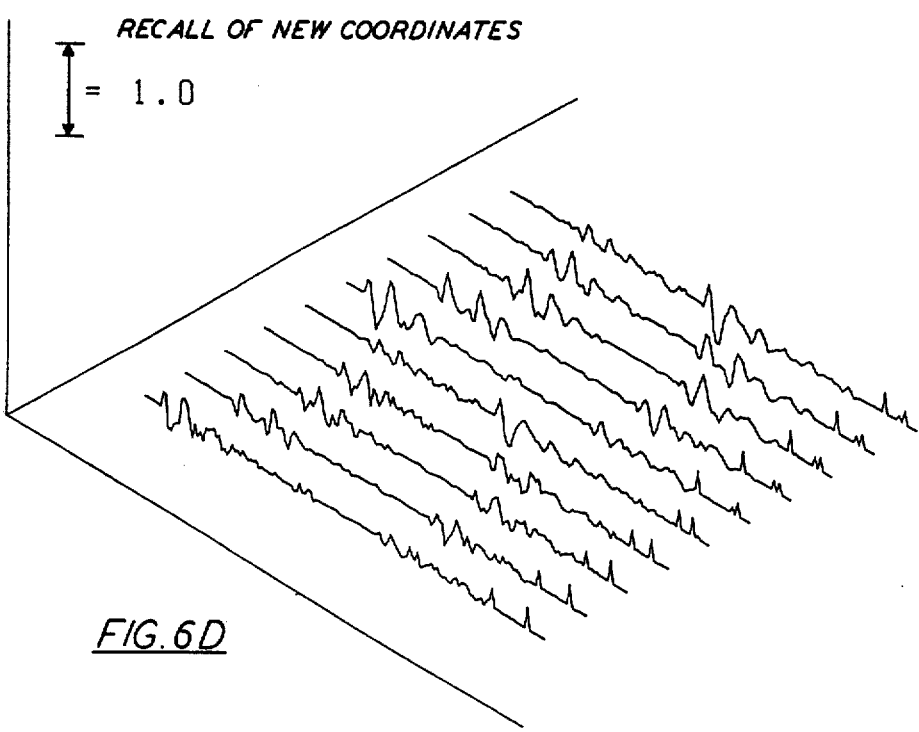
FIG. 6D shows the recalled signals of a second series of tests.

In a second series of tests, the recall signals represented in FIG. 6D were obtained. As in the previous experiments, the source location is correctly recovered. The recalled ball size is now accurately recovered for the smaller ball (6D1, ..., 6D5), while for the larger one (6D6, ..., 6D10), it can only be estimated from a comparison of the heights of the corresponding peaks in the waveforms.

Figure 7:
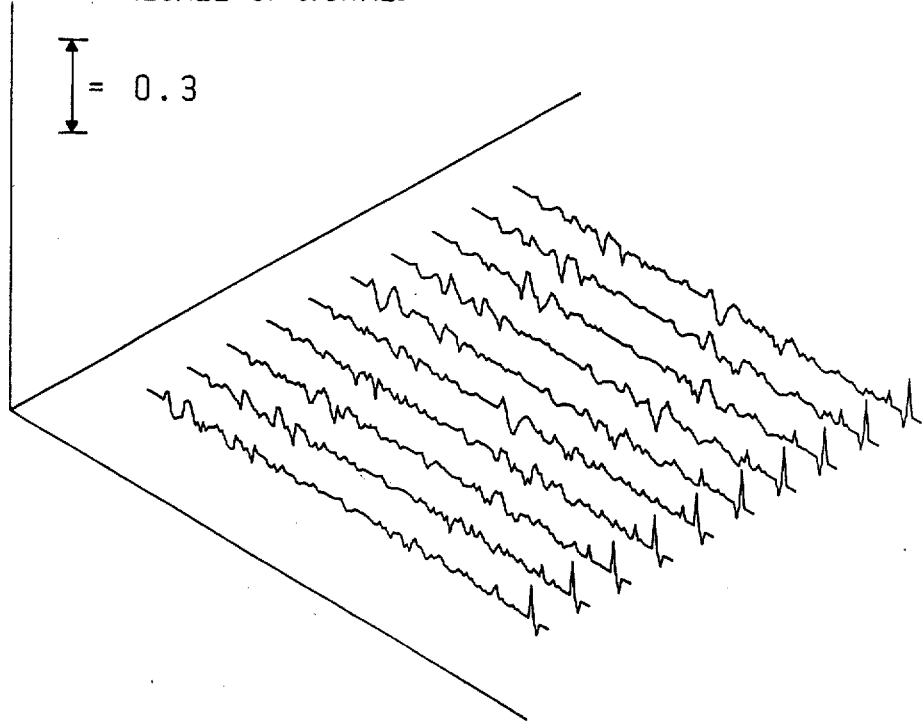
FIG. 7 shows the recall of the AE signals from only the input of the source coordinate data.

FIG. 7 shows the recall of the AE signals 7.1, ..., 7.10 from only the input of the source coordinate data or the recalled AE signals corresponding to specified location and ball size locations. In contrast to the previous experiment, the recall here is much better. This result is probably a consequence of the smaller number of patterns presented to the system during the learning process.

The third series of experiments involved a planar source location system consisting of four sensors, mounted in a square array whose length was 12 inches, or 0.3 m, on edge. The source location was in every test in the interior region of the array. The sampling frequency used in these measurements was 5.0 MHz and the signal source was the fracture of a pencil lead having a 0.3 mm diameter and a length of 2.5 mm. The digitized 1024-point signals detected at each sensor were reduced to 32 points, while the source position was encoded by two peaks in the coordinate portions of the pattern vector.

Figure 8A:
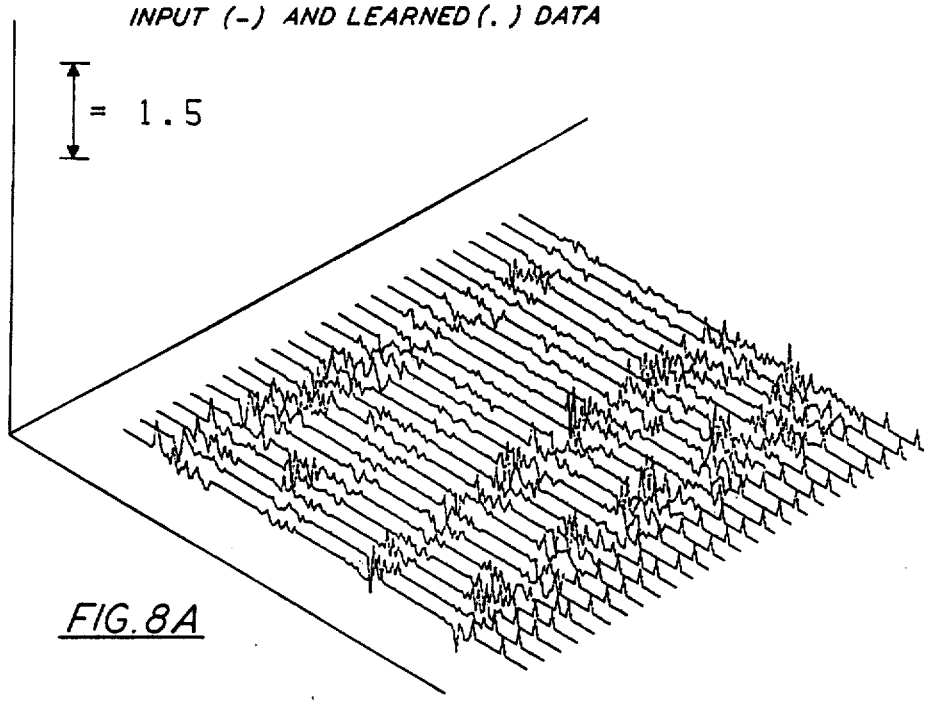
FIG. 8A discloses the set of input and learned data for a planar source location experiment.
Figure 8B:
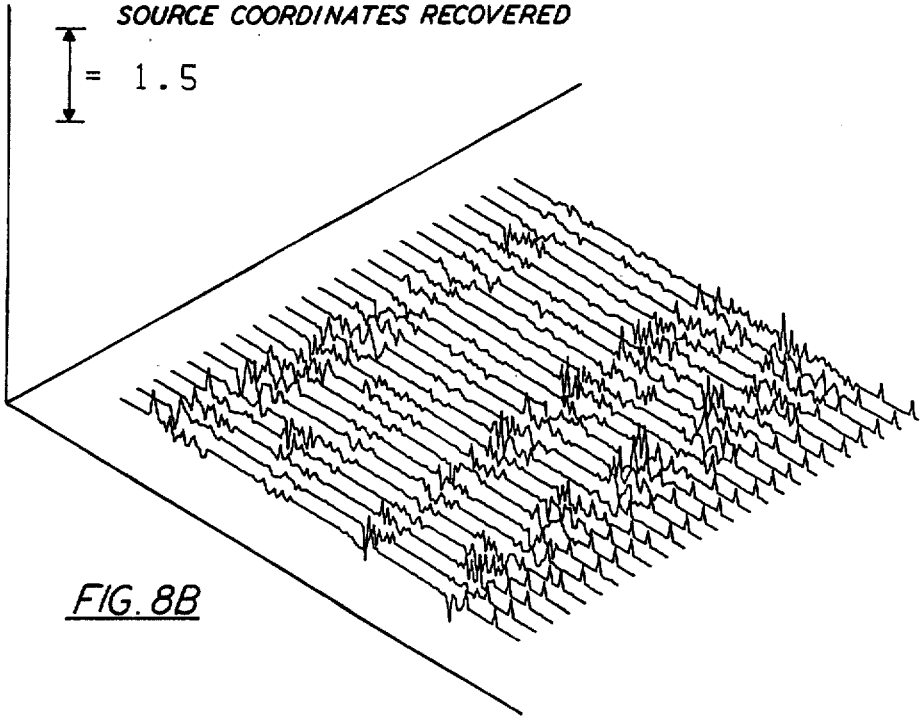
FIG. 8B shows the set of recall vectors recovering the coordinates for the planar source location experiment.

FIG. 8A describes the set of input and learned data and FIG. 8B shows the recalled vectors obtained from the AE signals, including the exact recall of the source coordinate points. This result is expected since the pattern vectors are nearly linearly independent to each other. T. Kohonen, "Self-organization and Associative Memory." The orthogonal property results, in part, from the high-frequency content of the pencil lead fracture present in the detected signals. The 32-fold reduction in data to meet the requirements of the available processing system probably also played a role. Because of this severe reduction of data, the reproducibility of signals in repeat experiments is not adequate, so that the dimensionality of the pattern vector should first be increased if higher resolution source location results are sought.

Referring now to FIG. 1, the neural network processor of the invention consists of an array of sensors (S), referred to as reference numeral 10, signal conditioner (SC) 12, neural network module (NN) 14, and the data output module (DO) 16.

The sensor array (S) 10 comprises two sub-arrays: $S_1$, $S_2$, ..., $S_N$ and $S_{N+1}$, $S_{N+2}$, ..., $S_{N+M}$ which are used to detect the emitted wave field and to characterize the source quantity, respectively. The signals from the sensor array (S) 10, given by $v_1, v_2, \ldots, v_N; g_1, g_2, \ldots, g_M$ are input to the signal conditioner (SC) 12, where they are transformed into a series of data comprising the multi-component pattern vector, X. If the source is not quantitatively characterized by signals from sensors, but is instead described phenomenologically, then the corresponding information channels must be supported by a device for manual inscription of the source components, $g_1, g_2, \ldots, g_M$, as for example via a keyboard.

Signal conditioner (SC) 12 is selected with respect to subsequent processing in neural network module (NN) 14. If the processing is via a digital computer, signal conditioner (SC) 12 may include amplifiers, filters and digitizers, not shown, which transform the input signals into a discrete series of digitized data comprising the components of the pattern vector. If the neural network (NN) 14 is implemented in analog hardware, then signal conditioner (SC) 12 includes the amplifiers and delay lines whose output is the multi-component, time-dependent pattern vector, X.

It is also advantageous for signal conditioner (SC) 12 to incorporate a self-calibration module so that the normalization of the pattern vectors can be obtained.

Neural network module (NN) 14 includes two essential components: a memory 16 and a multi-component subtractor 18. Memory 16 represents an adaptive system whose response function is described by the weighting matrix W. In neural network module (NN) 14, the pattern vector X is input to both memory 16 and to the positive input of subtractor 18. The response from memory 16 is described by a recall vector, $Y = WX$, which is applied to the negative input of subtractor 18. The output from subtractor 18 represents the vector, $V = X - Y = X - WX$. The novelty V is fed back into memory 16 to cause adaptative changes of matrix elements thereof, according to the chosen learning rule.

A switch 19 is shown in Recall position in the Figure. Switch 19 is bistable and can also be set to Learning position, as appropriate.

The output from neural network module (NN) 14 can be either recall vector, Y, or novelty vector, V, or both. The output is connected to a data output device (DO) 20 for display of the results and for data storage.

The neural network processor can operate in two different modes called learning and recall. During learning, novelty vector V is fed back to memory 16 to cause its adaptive change from W=0. Several learning rules leading to the same final result are applicable, the two simplest being given by $$\frac{dW}{dt} = V_k V_k^T \text{ or } \frac{dW}{dt} = V_k X_k^T$$

where k is the index of the presented pattern. During the recall, the feedback is turned off to prevent altering the previously formed memory.

When the system is simulated on a digital computer, the changes of the memory during learning are done in discrete steps so that learning in this case corresponds to an iterative procedure. If the system is implemented in analog hardware, the memory can be changed continuously as the pattern vectors are presented to the system.

Although the elements of the complete neural signal processor may be discrete components, an implementation comprising parallel processors offers the inherent advantages of speed, miniaturization and the ability to analyze problems of large dimensional complexity.

In the neural-like processing system of present the invention, as hereinbefore described, the entire memory matrix is adaptively changed simultaneously in the learning phase. A feedback to the memory is thus caused by contributions coming from the auto- as well as cross-correlation portions of the signals. An improved learning procedure, but with a more complicated system, can be realized if the auto- and cross-correlation portions are formed separately adaptively. In this case, the system learns to reproduce more exactly the signals in the recall using only the cross-correlation portions of the memory. This is of importance primarily for the recall of AE signals from encoded source information. When similar signals are compared, an auto-associative recall is needed.

For more reliable and practical applications it will be important to retain, in the process, information about signal amplitudes. In the aforedescribed examples, information about the signal amplitudes was lost during the normalization of the vectors.

In the system of the invention, the pattern vectors are treated as being constant, while the memory matrix adapts to them in successive learning steps. By this approach, the spatial and temporal dependence of an acoustic emission phenomenon is discarded. In a more exact approach, corresponding to a parallel, optimal filtering, this deficiency is avoided. I. Grabec, "Optimal Filtering of Transient AE Signals" and I. Grabec, "Development of a Force Transducer for AE Analysis".

However, problems remain in the practical application of a neural network-like system. The principal problem is related to the time-invariant operation. It has been avoided in the aforedescribed experiments by use of a synchronizing trigger pulse. A practical processing system should learn and recognize the signal properties, irrespective of the origin of the time record. This is not the case in the aforedescribed system. It is suggested that the problem can be solved by a proper pre-processing of the signals in the frequency domain. T. Kohonen, "Self-organization and Associative Memory".

Another problem is related to the training of the system. In order to obtain a reliable recall, signals from source points sufficiently evenly distributed over that region of the structure which is to be closely monitored have been used. Because the training generally involves a large amount of experimental work, the question arises if the system could be trained by only some representative patterns, while the missing information could be substituted algorithmically by a proper interpolation or extrapolation procedure. A solution of this problem would also help to circumvent the difficulties related to the experimental simulation of AE sources in the interior of a structure to be monitored.

The aforedescribed simulations demonstrate that a simple auto-associative system can be used for an approximate analysis of AE signals to recover specific characteristics of a source of emission or missing signal elements of a pattern vector. It was found that the auto-associative recall may not be perfect, because of similarities between some of the vectors comprising the learning set, and because of noise present in the experimental time records. Nevertheless, the most expressive properties of the recall vector were shown to correspond to the original ones.

It should be possible to carry out the learning process and the corresponding auto-associative recall hereinbefore described on an analog electronic neural network composed of operational amplifiers and multipliers. D. Farmer, A. Lapedes, N. Packard and B. Wendroff, Eds., "Evolution, Games and Learning", Physica, 22D, North-Holland, Amsterdam (1986) and J. J. Hopfield and D. W. Tank, "Computing with Neural Circuits: A Model", Science, 233, 625–633 (1986). Because of its real-time, parallel operations, such a network should be superior in many practical applications and it appears that it would be advantageous for future AE signal processing systems to incorporate such neural networks.

The principal problems of the aforedescribed system are related to loss of the spatial and temporal information of the acoustic emission phenomenon. Possible approaches for dealing with these problems have been described. Higher resolution and recovery of additional information about a source is possible, provided that higher-dimensioned input vectors and a correspondingly larger memory matrix are utilized.

Regardless of the aforementioned problems, the principal advantage of the system of the invention is that it is completely independent of any elastodynamic theory, or inversion algorithm, although it is capable of yielding quantitative results. Utilizing the detailed features of a detected signal, the entire procedure depends only on that information presented to the system during the learning process. The applicability of such a procedure is not restricted to the AE system described herein, or to acoustic systems in general.

Just as learning can be performed by trained personnel who have no deep understanding of any underlying theoretical basis, so also can the system of the invention operate. The use of a neural-like signal processing system can form the basis for new instrumentation having application to many other intelligent non-destructive materials test and monitoring systems, as well as systems with medical and seismological applications. A future development can be an electronic hardware implemented neural network to process the signals detected with multiple and multi-sensory arrays. D. Farmer et al, "Evolution, Games and Learning" and J.

J. Hopfield et al, "Computing with Neural Circuits: A Model".

Although learning in the proposed invention can only be achieved by a proper non-linear adaptation by which the dynamical Gren's function and its inverse are mapped to the weighting matrix of the neural network, in the analysis mode, it operates as a linear system which is appropriate for obtaining solutions to a broad range of inverse problems.

The invention also differs from earlier ones in the structure of neural network module (NN) 14, as well as in the structure of the complete signal analyzer. Without proper signal conditioning, a correct analysis of waveforms is not possible.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

What is claimed is:

1. A neural-like processing method for analyzing acoustic emission signals that emanate from a medium under test, comprising the steps of:
   (a) obtaining acoustic emission signals emanating from a medium under test to which a known source signal has been applied;
   (b) encoding said known source signal with a descriptor characteristic of said known source signal, such as its location with respect to the medium, its strength, and its time function;
   (c) concatenating said obtained acoustic emission signals to form a series chain of acoustic emission signals defining a pattern vector representative of said medium under test;
   (d) appending said known source descriptor to said series chain;
   (e) introducing said pattern vector to a storage medium;
   (f) repeating steps (a) through (e) a number of times in order to establish a data base characterizing the medium and its response to known source signals; and
   (g) synthesizing from said data base in said storage medium, characteristics of an unknown source based upon simulated acoustic emissions, or characteristics of acoustic emissions based upon a simulated unknown source.

2. The method of claim 1, wherein a descriptor comprises characteristics indicative of said medium.

3. The method of claim 1, further comprising the step of:
   (h) detecting a difference between a newly generated pattern vector and a pattern vector recalled from said storage medium.

4. The method of claim 1, wherein information introduced to said storage medium is statistically weighted.

5. The method of claim 1, wherein said source signals comprises at least one of magnetic, electromagnetic, radio, sonar and piezoelectric signals.

6. The method of claim 1, wherein a plurality of known source signals are applied to said medium in step (a), and further wherein a plurality of descriptors are appended to said pattern vector of step (d).

7. The method of claim 6, wherein the known source signals applied to said medium under test are propagated through said medium and said obtained acoustic emission signals utilized to generate a pattern vector are obtained by the additional step of:
   (h) placing a number of sensors about said medium under test.

8. The method of claim 7, wherein a descriptor comprises characteristics indicative of a sensor.

9. A neural-like processing method for analyzing emission signals that emanate from a medium under test, comprising the tests of:
   (a) obtaining emission signals emanating from a medium under test to which a known source signal has been applied;
   (b) encoding said known source signal with a descriptor characteristic of said known source signal;
   (c) concatenating said obtained emission signals to form a series chain of emission signals defining a pattern vector representative of said medium under test;
   (d) appending said known source descriptor to said series chain;
   (e) introducing said pattern vector to a storage medium;
   (f) repeating steps (a) through (e) a number of times in order to establish a data base characterizing the medium and its response to known source signals; and
   (g) synthesizing from said data base in said storage medium characteristics of an unknown source based upon simulated emissions, or characteristics of emissions based upon a simulated unknown source.

10. The method of claim 9, wherein a plurality of known source signals are applied to said medium in step (a), and further wherein a plurality of descriptors are appended to said pattern vector of step (d).

11. The method of claim 9, wherein a descriptor comprises characteristics indicative of said medium.

12. The method of claim 9, further comprising the step of:
   (h) detecting a difference between a newly generated pattern vector and a pattern vector recalled from said storage medium.

13. The method of claim 9, wherein information introduced to said storage medium is statistically weighted.

14. The method of claim 9, wherein said source signals comprises at least one of magnetic, electromagnetic, radio, sonar and piezoelectric signals.

15. The method of claim 9, wherein the known source signals applied to said medium under test are propagated through said medium and said obtained emission signals utilized to generate a pattern vector are obtained by the additional step of:
   (h) placing a number of sensors about said medium under test.

16. The method of claim 15, wherein a descriptor comprises characteristics indicative of a sensor.

17. A neural-like processing method for analyzing emission signals that emanate from a medium under test, comprising the steps of:
   (a) concatenating obtained emission signals to form a series chain of emission signals defining a pattern vector representative of a medium under test;
   (b) introducing said pattern vector to a storage medium; and
   (c) synthesizing from said storage medium, characteristics of an unknown source whose signal is applied to said medium under test based upon simulated emissions, or characteristics of emissions based upon a simulated unknown source whose signal is applied to said medium under test.

18. The method of claim 17, further comprising the step of:
    (d) detecting a difference between a newly generated pattern vector and a pattern vector recalled from said storage medium.

19. The method of claim 17, wherein information introduced to said storage medium is statistically weighted.

20. The method of claim 17, wherein the known source signals applied to said medium under test are propagated through said medium and said obtained emission signals utilized to generate a pattern vector are obtained by the additional step of:
    (d) placing a number of sensors about said medium under test.

21. The method of claim 20, wherein a descriptor comprises characteristics indicative of a sensor.

22. The method of claim 17, wherein a plurality of known source signals are applied to said medium and further wherein a plurality of descriptors representative of said known source are appended to said pattern vector of step (a).

23. The method of claim 22, wherein a descriptor comprises characteristics indicative of said medium.

24. The method of claim 22, wherein said source signals comprises at least one of magnetic, electromagnetic, radio, sonar and piezoelectric signals.

25. A neural-type system for analyzing emission signals from a medium under test, comprising:
    an array of sensors located about a medium under test, for generating a plurality of emission signals;
    a signal conditioner connected to said array of sensors for receiving said emission signals and utilizing said emission signals to generate a pattern vector, said generated pattern vector comprising a concatenation of said emission signals and an appended descriptor characterizing a source for stimulating said array of sensors to generate said plurality of emission signals;
    a neural network module connected to said signal conditioner for weighting said pattern vector, and generating an output comprising an adaptively changed pattern vector; and
    a data output device connected to said neural network module for receiving and storing an output of said neural network module.

26. The neural-type system of claim 25, wherein said data output device comprises a display for displaying vector information.

27. The neural-type system of claim 25, wherein said signal conditioner comprises at least one of: amplifiers, filters, and digitizers, and combinations thereof.

28. The neural-type system of claim 25, wherein said signal conditioner comprises at least one amplifier and delay lines.

29. The neural-type system of claim 25, wherein said signal conditioner comprises a self-calibration module.

30. The neural-type system of claim 25, wherein said neural network module comprises a memory and a multi-component subtractor.

31. The neural-type system of claim 25, wherein said array of sensors comprises a first sub-array for detecting an emitted wave field, and a second sub-array for characterizing a quantity of a source input applied to said medium under test.

32. The neural-type system of claim 31, further comprising a keyboard connected to said signal conditioner, and wherein signals from said second sub-array are substituted for by signals generated by said keyboard.

33. The neural-type system of claim 25, wherein said neural network module is operative in a learning mode "a" and a recall mode "b".

34. The neural-type system of claim 33, wherein said neural network module comprises a bistable switch for switching between "a" and mode "b".

* * * * *

UNITED STATES PATENT AND TRADEMARK OFFICE
CERTIFICATE OF CORRECTION

PATENT NO. : 4,979,124
DATED : December 18, 1990
INVENTOR(S) : Wolfgang H. Sachse, et. al.

It is certified that error appears in the above-indentified patent and that said Letters Patent is hereby corrected as shown below:

Column 1, line 7, delete "National Institute of Health" and substitute therefor --National Science Foundation--.

Signed and Sealed this

First Day of August, 1995

Attest:

BRUCE LEHMAN

Attesting Officer     Commissioner of Patents and Trademarks